US011584802B2

(12) United States Patent
Yan et al.

(10) Patent No.: US 11,584,802 B2
(45) Date of Patent: Feb. 21, 2023

(54) HEXOKINASE 2-SPECIFIC INHIBITORS FOR USE IN ACUTE CENTRAL NERVOUS SYSTEM INJURY

(71) Applicant: Guangzhou Cellprotek Pharmaceutical Co., Ltd., Guangdong (CN)

(72) Inventors: Guangmei Yan, Guangdong (CN); Wei Yin, Guangdong (CN); Yuan Li, Guangdong (CN); Bingzheng Lu, Guangdong (CN); Longxiang Sheng, Guangdong (CN)

(73) Assignee: Guangzhou Cellprotek Pharmaceutical Co., Ltd., Guangdong (CN)

( * ) Notice: Subject to any disclaimer, the term of this patent is extended or adjusted under 35 U.S.C. 154(b) by 124 days.

(21) Appl. No.: 16/488,011

(22) PCT Filed: Feb. 6, 2018

(86) PCT No.: PCT/CN2018/075401
§ 371 (c)(1),
(2) Date: Aug. 22, 2019

(87) PCT Pub. No.: WO2018/153244
PCT Pub. Date: Aug. 30, 2018

(65) Prior Publication Data
US 2020/0392250 A1 Dec. 17, 2020

(30) Foreign Application Priority Data
Feb. 23, 2017 (CN) .......................... 201710099324.9

(51) Int. Cl.
C07K 16/40 (2006.01)
A61P 25/00 (2006.01)
C12N 15/113 (2010.01)
A61K 45/06 (2006.01)

(52) U.S. Cl.
CPC .............. C07K 16/40 (2013.01); A61P 25/00 (2018.01); C12N 15/1137 (2013.01); A61K 45/06 (2013.01)

(58) Field of Classification Search
CPC ...... C07K 16/40; A61P 25/00; C12N 15/1137; A61K 45/06
See application file for complete search history.

(56) References Cited

FOREIGN PATENT DOCUMENTS

| CN | 106344573 A | 1/2017 |
| CN | 106860867 A | 6/2017 |
| WO | WO-2016/126618 A1 | 8/2016 |
| WO | WO-2016/196890 A1 | 12/2016 |

OTHER PUBLICATIONS

Hu et al., Signal Transduction and targeted Therapy, 2020, 5:101.*
Lam et al., Molecular Therapy-Nucleic Acids, 2015, 4:e252.*
Cheng et al., "Adjudin—A Male Contraceptive with Other Biological Activities", Recent Pat Endocr Metab Immune Drug Discov., 2015, Vo. 9, No. 2, pp. 63-73.
Li et al., "Hexokinase 2-Dependent Hyperglycolysis Driving Microglial Activation Contributes to Ischemic Brain Injury", Journal of Neurochemistry 2018, vol. 144 pp. 186-200.
Chambers et al., "The Anti-Trypanosomal Agent Lonidamine Inhibits Trypanosoma Brucie Hexokinase 1", Molecular and Biochemical Parasitology, vol. 158, 2008, pp. 202-207.
Floridi et al., "Effect of Ionidamine on the Energy Metabolism of Ehrlich Ascites Tumor Cells", Cancer Research, vol. 41, Nov. 1981, pp. 4661-4666.
Garcia et al., "Unlocking the Potential of HK2 in Cancer Metabolism and Therapeutics", Current Medicinal Chemistry, 2019, vol. 26, pp. 7285-7322.
Liu et al., "Adjudin Protects Against Cerebral Ischemia Reperfusion Injury by Inhibition of Neuroinflammation and Blood-Brain Barrier Disruption", Journal of Neuroinflammation, 2014, vol. 11, No. 107, ten (10) pages.
Rogers et al., "Correlation Between Motor Impairment and Infarct Volume After Permanent and Transient Middle Cerebral Artery Occlusion in the Rat", Stroke, vol. 28, Issue 10, Oct. 1997, pp. 2060-2066.
Schmeisser et al., "Lonidamine Extends lifespan of Adult Caenorhabditis Elegans by Increasing the Formation of Mitochondrial Reactive Oxygen Species", Horm Metab Res, 2011, vol. 43, 687-692.
Shao et al., "Adjudin Attenuates Lipopolysaccharide (LPS)- and Ischemia-Induced Microglial Activation", Journal Neuroimmunology, Jan. 15, 2013, 254 (0), pp. 83-90.
Slivka et al., "Cerebral Edema After Temporary and Permanent Middle Cerebral Artery Occlusion in the Rat", Stroke, vol. 26, Issue 6, Jun. 1995, pp. 1061-1066.
Tash et al., "Gamendazole, an Orally Active Indazole Carboxylic Acid Male Contraceptive Agent, Targets HSP90AB1 (HSP90Beta) and EEF1A1 (eEF1A), and Stimulates IIIa Transcription in rat Sertoli Cells", Biology of Reproduction, vol. 78, 2008, pp. 1139-1152.
Wang et al., The prevention and Treatment of Stroke Still Face Huge Challenges—Brief Report on Stroke Prevention and Treatment in China, Chinese Circulation Journal, Feb. 2019, vol. 34, No. 2, pp. 105-119, with English Abstract.
Xia et al., "A Sirtuin Activator and an Anti-Inflammatory Molecule-Multifaceted Roles of Adjudin and its Potential Applications for Aging-Related Diseases", Seminars in Cell & Development Biology, 2016, eight (8) pages total.
Xie et al., "Male Contraceptive Adjudin is a Potential Anti-Cancer Drug", Biochem Parmacol., Feb. 1, 2013, vol. 85, No. 3, pp. 345-355.
Gu et al., "Clk1 deficiency promotes neuroinflammation and subsequent dopaminer gic cell death through regulation of microglial metabolic reprogramming", Brain, Behavior, and Immunity,2016, doi: http://dx.doi.org/10.1016/j.bbi.2016.10.018 (43 pages).
Cheng et al., "Adjudin—A Male Contraceptive with Other Biological Activities", Recent Pat Endocr Metab Immune Drug Discov., 2015, 9(2), pp. 63-73.

(Continued)

Primary Examiner — Olga N Chernyshev
(74) Attorney, Agent, or Firm — Foley & Lardner LLP

(57) ABSTRACT

Provided are applications of a hexokinase 2-specific inhibitor in preparing a medicament for preventing and treating acute central nervous system injury.

3 Claims, 7 Drawing Sheets

Specification includes a Sequence Listing.

(56) References Cited

OTHER PUBLICATIONS

First Office Action issued in CN Application No. 201710099324.9 dated Jun. 13, 2019, 5 pages.
First Office Action issued in TW Application No. 107104211 dated Apr. 2, 2019, 4 pages.
International Search Report and Written Opinion issued in PCT Application No. PCT/CN2018/075401 dated May 8, 2018, 9 pages.
Lee et al., "Inhibition of Hexokinase Leads to Neuroprotection Against Excitotoxicity in Organotypic Hippocampal Slice Culture", Journal of Neuroscience Research, 2011, 89, pp. 96-107.
Sanchez-Alvarez et al., "Endothelin-1 stimulates the translocation and upregulation of both glucose transporter and hexokinase in astrocytes: relationship with gap junctional communication", Journal of Neurochemistry, 2004, 89, pp. 703-714.
Youngjeon Lee et al., "Therapeutically Targeting Neuroinflamation and Microglia After Acute Ischemic Stroke", BioMed Research International, vol. 2014, Article ID 297241, 9 (nine) pages, Jun. 25, 2014.
Hinrichs, Carina. "Exploring the anti-leukemic effect of the combination treatment with Valproic acid, Lonidamine and Mycophenolate mofetil in acute myeloid leukemia." MS thesis, The University of Bergen, 2015. pp. 1,17.

\* cited by examiner

SEQUENCE LISTING

```
<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: HK1 Forward Primers

<400> SEQUENCE: 1 gtagggtac gcttaggtgg                                                  20

<210> SEQ ID NO 2
<211> LENGTH: 20
<212> TYPE: DNA
<213> ORGANISM: Artificial Sequence
<220> FEATURE:
<223> OTHER INFORMATION: HK1 Reverse Primers

<400> SEQUENCE: 2
acccaggagt ccataaagcc                                                 20

<210> SEQ ID NO 3
<211> LENGTH: 20
<212> TYPE: DNA
<213> ORGANISM: Artificial Sequence
<220> FEATURE:
<223> OTHER INFORMATION: HK2 Forward Primers

<400> SEQUENCE: 3
gagaaagctc agcatcgtgg                                                 20

<210> SEQ ID NO 4
<211> LENGTH: 20
<212> TYPE: DNA
<213> ORGANISM: Artificial Sequence
<220> FEATURE:
<223> OTHER INFORMATION: HK2 Reverse Primers

<400> SEQUENCE: 4
tccatttgta ctccgtggct                                                 20

<210> SEQ ID NO 5
<211> LENGTH: 20
<212> TYPE: DNA
<213> ORGANISM: Artificial Sequence
<220> FEATURE:
<223> OTHER INFORMATION: HK3 Forward Primers

<400> SEQUENCE: 5
gctccgttga gagcagattt                                                 20

<210> SEQ ID NO 6
<211> LENGTH: 20
```

```
<212> TYPE: DNA
<213> ORGANISM: Artificial Sequence
<220> FEATURE:
<223> OTHER INFORMATION: HK3 Reverse Primers

<400> SEQUENCE: 6
ttgctgcaag cattccagtt                                          20

<210> SEQ ID NO 7
<211> LENGTH: 21
<212> TYPE: DNA
<213> ORGANISM: Artificial Sequence
<220> FEATURE:
<223> OTHER INFORMATION: PFKM Forward Primers

<400> SEQUENCE: 7
gtttggaagc ctctcctcct c                                        21

<210> SEQ ID NO 8
<211> LENGTH: 20
<212> TYPE: DNA
<213> ORGANISM: Artificial Sequence
<220> FEATURE:
<223> OTHER INFORMATION: PFKM Reverse Primers

<400> SEQUENCE: 8
gacggcagca ttcatacctt                                          20

<210> SEQ ID NO 9
<211> LENGTH: 20
<212> TYPE: DNA
<213> ORGANISM: Artificial Sequence
<220> FEATURE:
<223> OTHER INFORMATION: PFKL Forward Primers

<400> SEQUENCE: 9
cgcaaggtat gaatgctgct                                          20

<210> SEQ ID NO 10
<211> LENGTH: 20
<212> TYPE: DNA
<213> ORGANISM: Artificial Sequence
<220> FEATURE:
<223> OTHER INFORMATION: PFKL Reverse Primers

<400> SEQUENCE: 10
cgatggtcaa gtgtgcgtag                                          20

<210> SEQ ID NO 11
<211> LENGTH: 20
<212> TYPE: DNA
<213> ORGANISM: Artificial Sequence
<220> FEATURE:
<223> OTHER INFORMATION: PGK1 Forward Primers

<400> SEQUENCE: 11
cgagcctcac tgtccaaact                                          20

<210> SEQ ID NO 12
<211> LENGTH: 20
<212> TYPE: DNA
<213> ORGANISM: Artificial Sequence
<220> FEATURE:
<223> OTHER INFORMATION: PGK1 Reverse Primers
```

<400> SEQUENCE: 12
gtctgcaact ttagcgcctc                                              20

<210> SEQ ID NO 13
<211> LENGTH: 20
<212> TYPE: DNA
<213> ORGANISM: Artificial Sequence
<220> FEATURE:
<223> OTHER INFORMATION: PKM1 Forward Primers

<400> SEQUENCE: 13
cgtccgcagg tttgatgaga                                              20

<210> SEQ ID NO 14
<211> LENGTH: 20
<212> TYPE: DNA
<213> ORGANISM: Artificial Sequence
<220> FEATURE:
<223> OTHER INFORMATION: PKM1 Reverse Primers

<400> SEQUENCE: 14
ttcaaacagc agacggtgga                                              20

<210> SEQ ID NO 15
<211> LENGTH: 20
<212> TYPE: DNA
<213> ORGANISM: Artificial Sequence
<220> FEATURE:
<223> OTHER INFORMATION: PKM2 Forward Primers

<400> SEQUENCE: 15
ggctcctatc attgccgtga                                              20

<210> SEQ ID NO 16
<211> LENGTH: 20
<212> TYPE: DNA
<213> ORGANISM: Artificial Sequence
<220> FEATURE:
<223> OTHER INFORMATION: PKM2 Reverse Primers

<400> SEQUENCE: 16
aaggtacagg cactacacgc                                              20

<210> SEQ ID NO 17
<211> LENGTH: 20
<212> TYPE: DNA
<213> ORGANISM: Artificial Sequence
<220> FEATURE:
<223> OTHER INFORMATION: Actb Forward Primers

<400> SEQUENCE: 17
tgagctgcgt tttacaccct                                              20

<210> SEQ ID NO 18
<211> LENGTH: 20
<212> TYPE: DNA
<213> ORGANISM: Artificial Sequence
<220> FEATURE:
<223> OTHER INFORMATION: Actb Reverse Primers

<400> SEQUENCE: 18
tttgggggat gtttgctcca                                              20

<210> SEQ ID NO 19

```
<211> LENGTH: 21
<212> TYPE: DNA
<213> ORGANISM: Artificial Sequence
<220> FEATURE:
<223> OTHER INFORMATION: Il1b promoter primer (forward)

<400> SEQUENCE: 19
aggtcaaagg tttggaagca g                                        21

<210> SEQ ID NO 20
<211> LENGTH: 25
<212> TYPE: DNA
<213> ORGANISM: Artificial Sequence
<220> FEATURE:
<223> OTHER INFORMATION: Il1b promoter primer (reverse)

<400> SEQUENCE: 20
atggaagtct gtctgctcag tattg                                    25

<210> SEQ ID NO 21
<211> LENGTH: 21
<212> TYPE: DNA
<213> ORGANISM: Artificial Sequence
<220> FEATURE:
<223> OTHER INFORMATION: the sequences targeting HK2

<400> SEQUENCE: 21
gcgcaacatt ctcatcgatt t                                        21

<210> SEQ ID NO 22
<211> LENGTH: 21
<212> TYPE: DNA
<213> ORGANISM: Artificial Sequence
<220> FEATURE:
<223> OTHER INFORMATION: the sequences targeting HK2

<400> SEQUENCE: 22
aaatcgatga gaatgttgcg c                                        21

<210> SEQ ID NO 23
<211> LENGTH: 19
<212> TYPE: DNA
<213> ORGANISM: Artificial Sequence
<220> FEATURE:
<223> OTHER INFORMATION: control shRNA sequence

<400> SEQUENCE: 23
ttctccgaac gtgtcacgt                                           19
```

HEXOKINASE 2-SPECIFIC INHIBITORS FOR USE IN ACUTE CENTRAL NERVOUS SYSTEM INJURY

CROSS-REFERENCE TO RELATED APPLICATIONS

This application is a national stage entry under 35 U.S.C. § 371 of International Patent Application No. PCT/CN2018/075401 filed Feb. 6, 2018, which claims priority to Chinese Patent Application No. 201710099324.9 filed Feb. 23, 2017, the entire content of each of which is hereby incorporated by reference.

FIELD OF INVENTION

The present disclosure is in the field of biomedicine and relates to the uses of hexokinase 2-specific inhibitors in the prophylaxis and treatment of acute central nervous system (CNS) injury diseases.

BACKGROUND

Stroke, either ischemic or hemorrhagic, is an acute cerebrovascular disease with brain damage caused by burst of blood vessels in the brain or diminished blood supply due to vascular occlusion. Ischemic stroke accounts for about 85% of the total cases. Tissue plasminogen activator (t-PA) is an FDA approved drug for ischemic stroke. However, t-PA is only suitable for 3-6 hours after stroke, and there is also a risk of cerebral hemorrhage and cerebral edema after treatment. These defects make t-PA application very limited and very few patients benefit. Therefore, safe and effective drugs that can be used for the prophylaxis and treatment of acute ischemic stroke are highly anticipated.

The immune system-mediated inflammatory response following acute ischemic stroke is a widely studied therapeutic target. However, the results of clinical trials of drugs using this mechanism as therapeutic targets are not satisfactory. For example, Fingolimod and Natalizumab, both being agents directing to peripheral immune system inflammatory response, are effective in inhibiting the penetration of lymphocytes into brain parenchyma, but clinical trials have shown that stroke patients do not benefit from such treatment. Therefore, in-depth exploration of the central nervous system inflammatory response mediated by microglia after ischemia is expected to provide new therapeutic targets and strategies for the prophylaxis and treatment of acute ischemic stroke.

SUMMARY OF THE INVENTION

The present inventors screened a series of glycolytic pathway genes, and identified that the selective up-regulation of hexokinase 2 mediated the activation process of hypoxia-induced microglia. The inventors confirmed that a range of biologically active substances that have a selectively inhibitory activity on hexokinase 2 can inhibit the activation of hypoxia-induced microglia. Moreover, the inventors also found that both hexokinase 1- and 3-interferences cannot inhibit the activation of hypoxia-induced microglia.

Thus, an aspect of the invention provides use of a hexokinase 2-specific inhibitor in the preparation of a medicament for prophylaxis and treatment of an acute central nervous system injury.

In another aspect, the invention provides use of a pharmaceutical composition comprising a hexokinase 2-specific inhibitor in the preparation of a medicament for prophylaxis and treatment of an acute central nervous system injury.

In a further aspect, the invention provides a method for prophylaxis and treatment of an acute central nervous system injury disease comprising administering to a subject in need thereof a prophylactically or therapeutically effective amount of a hexokinase 2-specific inhibitor or a pharmaceutical composition comprising a hexokinase 2-specific inhibitor.

The present inventors discovered the neuroprotective effect of a hexokinase 2-specific inhibitor in the prophylaxis and treatment of acute central nervous system injury. Cytological and in vivo animal experiments indicated that selectively up-regulated expression of hexokinase 2 regulated activation of hypoxia-induced microglia and microglia-mediated neuroinflammatory responses after ischemia, whereas both hexokinase 2 selective inhibitors and gene knockdown significantly inhibited microglia-mediated inflammatory responses and thereby exerted neuroprotective effect.

DETAILED DESCRIPTION OF THE INVENTION

Figure 1:
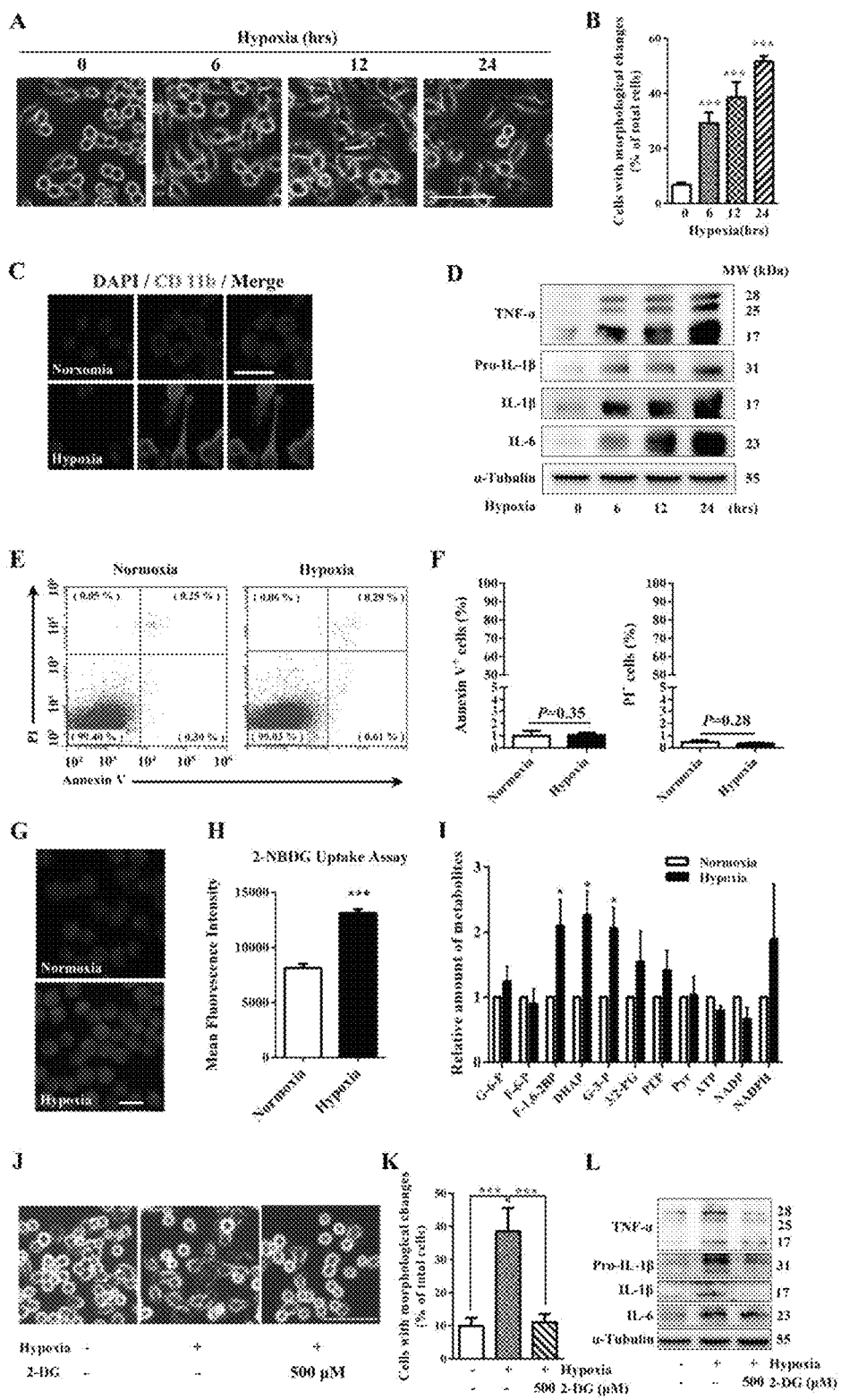
FIG. 1. Enhanced glycolytic flux is essential for hypoxia-induced microglial activation. (A) Representative images of BV 2 microglia subjected to hypoxic exposure for the indicated times. Scale bar, 100 μm (n=4). (B) Quantification of the percentages of microglial cells with morphological changes shown in (A) (n=4). (C) Hypoxia-induced microglial activation was verified by up-regulation of the molecular marker CD 11b. Scale bar, 25 μm (n=3). (D) Proinflammatory cytokines were markedly induced by hypoxia in BV 2 cells in a time-dependent manner (n=3). (E-F) Hypoxia had no effect on the viability of BV 2 cells. Flow cytometry analysis showing no significant increases in the numbers of Annexin V+ or PI+ cells after exposure to 1% oxygen for 24 hours (n=3). (G) Representative images of 2-[N-(7-nitrobenz-2-oxa-1,3-diazol-4-yl) amino]-2-deoxy-D-glucose (2-NBDG) uptake assays in cells incubated with 2-NBDG exposed to normoxia or hypoxia for 1 hour. Scale bar, 100 μm. (H) The mean fluorescence intensity in (G) was quantified using a multi-detection microplate reader (n=4). (I) Graphs illustrating key metabolites in the glycolytic pathway; the significantly enhanced metabolites were marked after exposure to hypoxia for 6 hours (n=4). (J-L) 2-DG, an inhibitor of the glycolytic pathway, significantly blocked microglia activation during hypoxia. (J) Phase contrast images of BV 2 cells subjected to 1% oxygen with or without 2-DG. (K) Decreased percentage of activated cells after the 2-DG treatment in (J). Scale bar, 50 μm (n=4). (L) The production of proinflammation cytokines was significantly impaired by 2-DG under hypoxia. *<0.05; <0.01; *<0.001.

The invention is now described in reference to following embodiments which should not be constructed as limiting to the scope of the invention. Any equivalent changes or variation made in accordance with the principle or spirit of the invention is contemplated within the scope of the invention.

In one aspect, the invention provides use of a hexokinase 2-specific inhibitor for the manufacture of a medicament for the prophylaxis and treatment of an acute central nervous system injury. The hexokinase 2-specific inhibitor as used herein refers to a substance capable of specifically or selectively inhibiting the biological activity of hexokinase 2 (also referred to as hexokinase II or HK2).

In some embodiments, the hexokinase 2 specific inhibitor comprises an antibody to hexokinase 2 or a fragment thereof. The antibody refers to a protein capable of specifically binding to hexokinase 2 and inhibiting or quenching the activity of hexokinase 2. A fragment of antibody can include, for example, Fab, Fab', (Fab')$_2$, and Fv. The production and purification of antibodies or fragments thereof are known in the art.

In some embodiments, a hexokinase 2 antibody of the invention may also exist in the form of an amino acid or nucleotide sequence encoding the antibody or an expression vector comprising the nucleotide or amino acid sequence. In some embodiments, the hexokinase 2 antibody described in the present invention may also be present in an expression vector or a host cell in the form of a fusion protein.

In some embodiments, the hexokinase 2 specific inhibitor comprises a substance capable of specifically inhibiting translation of mRNA of hexokinase 2, or a substance capable of specifically degrading mRNA of hexokinase 2, such as siRNA, shRNA, miRNA or its modifications, thereby interfering with the synthesis of hexokinase 2 by the RNAi mechanism. siRNA, shRNA or miRNA can be obtained by in vitro synthesis techniques, which are well known in the art. In some embodiments, the siRNA, shRNA or miRNA described in the present invention is present in a particular vector, such as in a cell.

In some embodiments, the acute central nervous system injury refers to a disease or condition of central nervous system damage caused by acute ischemia or hypoxia, including but not limited to, encephalon/spinal damage caused by acute spinal injury, brain trauma, retinal damage, hypoxic brain injury, acute ischemic brain injury, ischemic stroke, hypoxic stroke, neonatal hypoxic ischemic encephalopathy, toxic encephalopathy, acute cerebral infarction, lacunar infarction, transient ischemic attack, severe craniocerebral injury, cerebrospinal surgery and encephalon/spinal radiotherapy.

In another aspect, the invention provides use of a composition comprising a hexokinase 2-specific inhibitor for the manufacture of a medicament for the prophylaxis and treatment of an acute central nervous system injury disease.

In some embodiments, the hexokinase 2 specific inhibitors comprised in the composition are those as described above, and the composition may further comprise other hexokinase 2 inhibitors, including but not limited to, 2-deoxyglucose, Lonidamine, bromo-pyruvic acid, glucose 6-phosphate, Imatinib, 5-thio-glucose and methyl jasmonate.

A further aspect of the invention provides a method of preventing and treating an acute central nervous system injury, the method comprising administering to a subject in need thereof a prophylactically effective amount or a therapeutically effective amount of a hexokinase 2 specific inhibitor or a composition comprising a hexokinase 2 specific inhibitor.

In some embodiments, the subject is a mammalian subject, such as a human. The administration is performed subcutaneously, transdermally, intramuscularly, intravenously, intraarterially, sublingually, buccally, gastrointestinally or the like to a e.g. human subject. In some embodiments, a hexokinase 2 specific inhibitor (e.g., in nucleic acid form) can be administered to a subject being treated or prevented by gene therapy.

A further aspect of the present invention provides a method for preventing and treating an acute central nervous system injury, comprising selectively or specifically reducing or inactivating the activity of hexokinase 2 in a subject in need thereof. That reducing or inactivating the activity of hexokinase can be achieved, for example, by genetic engineering measures to reduce or eliminate the expression of the hexokinase 2 protein. An exemplary measure is to alter the hexokinase 2-encoding nucleotide sequence by site directed mutagenesis. Another exemplary means is interfering of the translation process of mRNA of hexokinase 2 by RNAi technology. Any method known to those skilled in the art to reduce the expression of a particular protein in a cell is contemplated for use in the methods of the invention.

EXAMPLES

The materials and methods employed in the present invention are conventional materials and methods, unless otherwise specified.

Example 1. Enhanced Glycolytic Flux is Essential for Hypoxia-Induced Microglial Activation Materials Mouse BV2 microglia cells, Dulbecco's modified Eagle's medium (DMEM, Gibco, 11965-118), fetal bovine serum (Gibco, 10099-141), 2-deoxy-D-glucose (Sigma-Aldrich, D8375), 2-[N-(7-nitrobenz-2-oxa-1,3-diazol-4-yl)amino]-2-deoxy-D-glucose (2-NBDG, Thermo Fisher Scientific, N13195), Annexin/PI detection kit (Biotool, B32115), flow cytometer (CytoFLEX S), laser scanning confocal microscope (Nikon A1 Spectral Confocal Microscope), anoxic chamber (Coy Laboratory Products).

Antibodies used in Western blot and immunofluorescence:
CD 11b antibody (Novus biologicals, NB 110-89474);
TNF-α antibody (CST, 11498);
IL-1β antibody (CST, 12507);
IL-6 antibody (Bioss, bs-6309R);
α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments. The cells in the hypoxic treatment group were placed in the Coy anoxic chamber with 1% 02, 5% $CO_2$, and 94% N2; other conditions were the same as normal culture conditions.

b) Protein extraction and proinflammatory cytokine protein expression assay: After incubated in 35 mm culture dishes and placed for 24 hours, the cells were subject to hypoxia treatment for indicated time. The total cellular protein was then extracted to detect protein expression of the proinflammatory cytokines TNF-α, IL-1β and IL-6.

c) CD 11b expression detected by Immunofluorescence: BV2 cells were seeded in a laser confocal-specific culture plate, and treated with hypoxia for 24 hours, fixed in 4% paraformaldehyde at room temperature for 20 minutes, and then washed three times with PBST for 5 minutes each time. After washing, CD 11b antibody diluted with DAKO antibody dilution was added and incubated overnight at 4° C. The next day, the samples were incubated with indicated fluorescently labeled secondary antibody at 37° C. for 1 hour. After the incubation, DAPI working solution was added for nuclear staining for 10 minutes. Samples were then washed three times with PBST and imaged using a laser confocal microscope.

d) 2-NBDG uptake assay: BV2 cells were seeded in a 96-well plate culture plate (black on the sides, transparent at the bottom) and cell medium was replaced with DPBS buffer containing 200 µM 2-NBDG after 24 hours. Cells were then cultured in normoxic or hypoxic conditions. After 1 hour of incubation, the medium was exchanged for fresh DPBS. Finally, images were captured and 2-NBDG uptake was quantified with a fluorescence microplate assay.

e) Annexin/PI staining: Cells were seeded in a 35 mm culture dish and cultured for 24 hours, and then cultured in hypoxic condition for 24 hours. The cells were harvested with 0.25% trypsin and stained by Annexin and PI dyes following the instructions provided by the manufacturer. Flow cytometry analysis was performed after 30 minutes to detect whether hypoxia caused cell death.

f) Metabolite extraction and profiling: BV2 cells were seeded in a 60 mm culture dishes and cultured for 24 hours and then cultured in normoxic or hypoxic conditions for 6 hours. For metabolite profiling, metabolites were extracted using 1.5 mL of ice-cold 80% methanol. After incubation at −80° C. for 30 minutes, cells were scrapped and centrifuged at 14, 000 g for 15 minutes at 4° C. The upper methanol/water phase were transferred into new tubes and incubated at −80° C. for another 30 minutes. The upper phases were centrifuged and dried under nitrogen gas and dried samples were stored at −80° C. prior to LC-MS analysis.

Results

As shown in FIG. 1A, hypoxia stimulation led to profound morphological changes in BV 2 cells, with enlarged cell bodies and filopodia or lamellipodia formation being observed. The morphological changes were time-dependent and microglial cells with morphological changes increased to about 52% of total cells after 24 hours of hypoxia exposure (FIG. 1B). Also, enhanced expression of CD 11b, a molecular marker of microglial activation, after 24 hours of hypoxia exposure were observed. In addition, as shown in FIG. 1D, productions of pro-inflammatory cytokines TNF-α, IL-1β and IL-6 were markedly induced in a time-dependent manner. Notably, exposure to 1% oxygen for 24 hours caused no obvious cell death (FIGS. 1E and 1F). The results above indicated that hypoxia exposure led to an inflammatory activated phenotype of microglia.

Aerobic glycolysis pathway in BV2 cells were significantly elevated after hypoxia exposure. As depicted in FIGS.

1G and 1H, 2-NBDG uptake was increased by 1.6-fold after 1 hour of hypoxic exposure. Metabolic profiling also showed a significantly elevated abundance of metabolic intermediates of the glycolytic pathway after 6 hours of hypoxic exposure, including fructose-1, 6-biphosphate, dihydroxyacetone phosphate and glyceraldehyde 3-phosphate (G-3-P) (FIG. 1I). In the presence of 500 μM 2-deoxyglucose (2-DG), an effective inhibitor of glycolysis, the percentage of BV 2 cells with activated morphological changes was significantly decreased (FIGS. 1J-L). Collectively, these data demonstrate that enhanced glycolysis is essential for microglial activation after hypoxia exposure.

Example 2. Upregulation of Hexokinase Family Members was Involved in the Microglial Activation after Hypoxia Exposure Materials Mouse BV2 microglia cell line, primary cultured mouse microglia, high glucose DMEM medium (Gibco, 11965-118), fetal bovine serum (Gibco, 10099-141), RNA extraction reagent TRIzol (Thermo Fisher Scientific, 15596-018), RNA quantification kit (Thermo Fisher Scientific, Q10211), SuperReal qPCR PreMix (SYBR Green) (Tiangen, FP202-01), real-time PCR system (Applied Biosystems), anoxic chamber (Coy Laboratory Products)

Antibodies used in Western blotting:
Hexokinase 1 antibody (Abcam, 150423),
Hexokinase 2 antibody (CST, 2867s),
Hexokinase 3 antibody (Santa Cruz, sc-28890),
α-Tubulin antibody (Bioworld, AP0064).

The following mouse gene primer sequences were used in real-time PCR.

| Primers | Forward | Reverse |
|---|---|---|
| HK1 | GTAGGGGTACGCTTAGGTGG | ACCCAGGAGTCCATAAAGCC |
| HK2 | GAGAAAGCTCAGCATCGTGG | TCCATTTGTACTCCGTGGCT |
| HK3 | GCTCCGTTGAGAGCAGATTT | TTGCTGCAAGCATTCCAGTT |
| PFKM | GTTTGGAAGCCTCTCCTCCTC | GACGGCAGCATTCATACCTT |
| PFKL | CGCAAGGTATGAATGCTGCT | CGATGGTCAAGTGTGCGTAG |
| PGK1 | CGAGCCTCACTGTCCAAACT | GTCTGCAACTTTAGCGCCTC |
| PKM1 | CGTCCGCAGGTTTGATGAGA | TTCAAACAGCAGACGGTGGA |
| PKM2 | GGCTCCTATCATTGCCGTGA | AAGGTACAGGCACTACACGC |
| Actb | TGAGCTGCGTTTTACACCCT | TTTGGGGATGTTTGCTCCA |

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments.

For the isolation and culture of primary microglia, cells were isolated from newborn C57BL/6J mice. Briefly, cerebral cortices devoid of meninges and blood vessels were dissociated from P0-2 mice and digested by 0.125% trypsin at 37° C. for 15 minutes. The digestion was terminated by addition of DMEM containing 10% FBS and isolated single cells were seeded in culture dishes. After the mixed cultures became confluent, microglia were separated from other cell types by slight shaking and purification was identified by the microglial-specific marker CD 11b.

b) Total protein extraction and hexokinase family proteins expression assay: Cells were seeded in 35 mm culture dishes for 24 hours, and stimulated with hypoxia for indicated time. The total protein was then extracted to detect protein expressions of the hexokinase family.

Results

Figure 2:
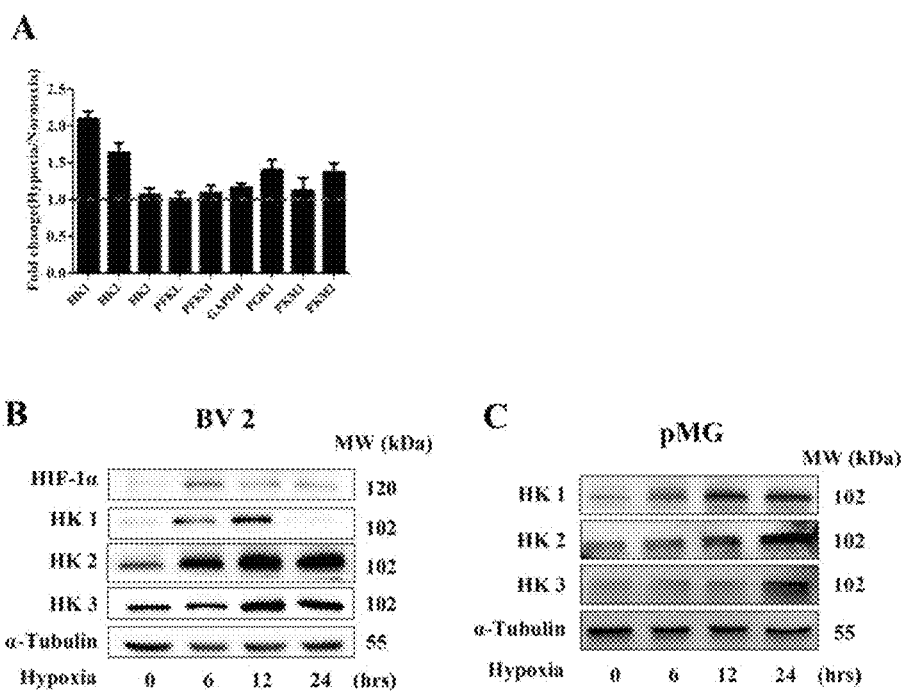
FIG. 2. Up-regulated expression of hexokinase family members was involved in the process of hypoxia-induced microglia activation. (A) Assays of the mRNA levels of enzymes by qRT-PCR. Graphs showing an overall increase in mRNA levels of these genes under hypoxia for 6 h (n=3). (B-C) HK1, HK2, and HK3 protein levels in BV 2 and primary microglia (pMG) cells subjected to hypoxia for the indicated times (n=4).
Figure 3:
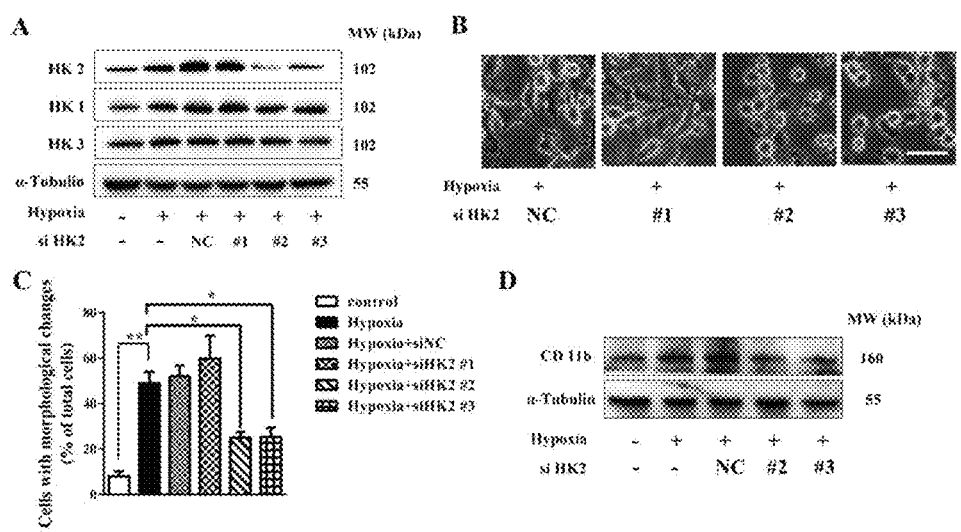
FIG. 3. Hexokinase 2 interference effectively inhibited hypoxia-activated microglia. (A) Specific HK2 knockdown was sufficient to block the activated phenotype of BV 2 microglia (n=3). The indicated protein levels were assayed by Western blot after BV 2 cells were transfected with or without HK2 siRNAs for 24 h and stimulated with hypoxia for another 24 hours. (B) Transfection of different HK2 interfering fragments into BV2 cells effectively repress the morphological changes induced by hypoxia. (C) Decreased percentage of microglia with activated morphologies in HK2-knockdown cells under hypoxia. (D) HK2 knockdown markedly repressed the expression of CD 11b.
Figure 4:
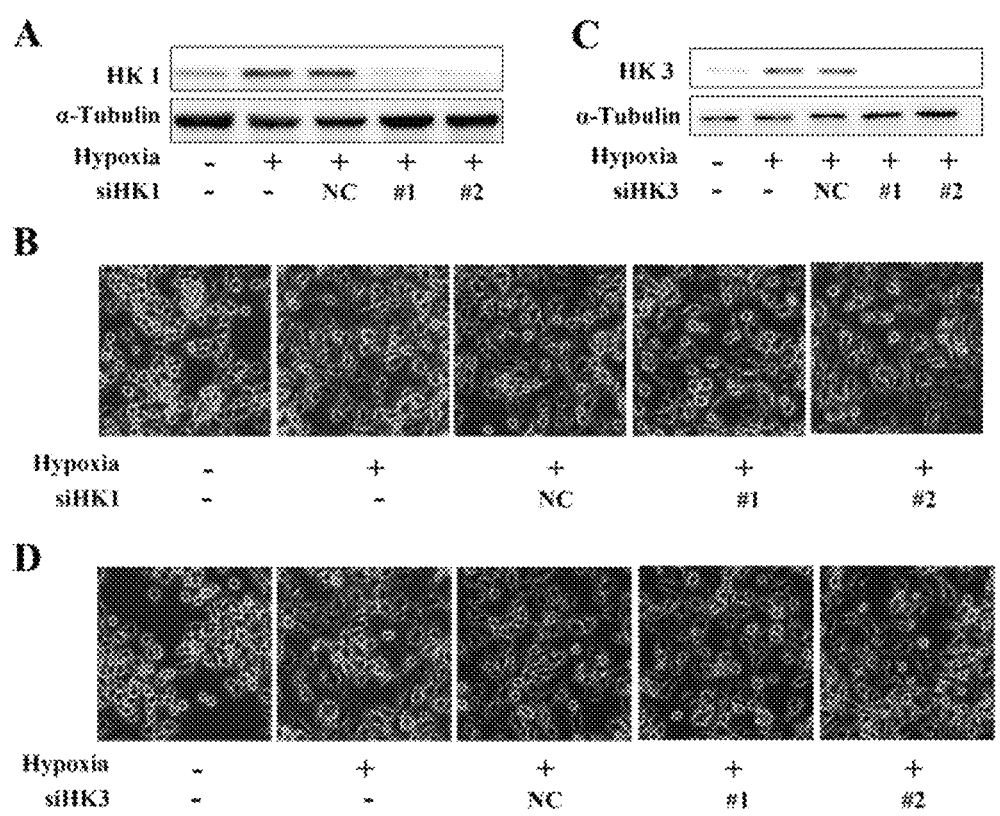
FIG. 4. Neither HK1 nor HK3 interference could repress the hypoxia-induced activation of microglia. The hypoxia-induced activation related microglia morphological changes (B and D, n=3) could not be effectively repressed by HK1 and HK3 interfering fragments, respectively (A and C).

After 6 hours of hypoxia, an overall up-regulation of the mRNA levels of these enzymes was detected. All three HK isoforms tested exhibited significantly increased mRNA expression (FIG. 2A). Further results showed protein expression of these isoforms also exhibited transient or sustained increases in BV 2 (FIG. 2b) and primary microglia cells (FIG. 2c).

Example 3 Hexokinase 2, Instead of Other Hexokinase Family Members, Mediated Hypoxia-Induced Activation of Microglia (1) Hexokinase 2 Interference could Effectively Inhibit the Hypoxia-Induced Activation Process of Microglia Materials Mouse BV2 microglia cell line, primary cultured mouse microglia, high glucose DMEM medium (Gibco, 11965-118), fetal bovine serum (Gibco, 10099-141), siRNA fragments, siRNA transfection reagent (Lipofectamine RNAiMAX Reagent, Thermo Fisher Scientific, 13778-500), inverted phase contrast microscope (Nikon ECLIPSE Ti Microscope), laser confocal microscope (Nikon A1 Spectral Confocal Microscope), anoxic chamber (Coy Laboratory Products).

Antibodies used in Western blotting:
Hexokinase 1 antibody (Abcam, 150423),
Hexokinase 2 antibody (CST, 2867s),
Hexokinase 3 antibody (Santa Cruz, sc-28890),
CD 11b antibody (Novus biologicals, NB 110-89474),
α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments.

b) RNA interference: Cells were seeded in a 35 mm culture dish for 24 hours. Short-interfering RNAs (siRNAs) were transfected with RNAiMAX Reagent. Scrambled RNA was used as a control. In total, 50 nM siRNAs were transfected into the cultures, and after 12 hours, the medium was replaced with fresh medium. Cells were then stimulated with hypoxia for 24 hours to detect the expression level of the indicated proteins.

Results

As shown in FIGS. 3A-3D, silencing HK2 expression using different fragments led to significant inhibition of the activated morphologies of microglia, which was also accompanied by the diminished expression of CD 11b. Notably, the siRNAs targeting HK2 had no effect on HK1 and HK3 expression.

(2) Hexokinase 1 and Hexokinase 3 Interference could not Inhibit Hypoxia-Induced Activation of Microglia Materials Mouse BV2 microglia cell line, high glucose DMEM medium (Gibco, 11965-118), fetal bovine serum (Gibco, 10099-141), siRNA fragments, siRNA transfection reagent (Lipofectamine RNAiMAX Reagent, Thermo Fisher Scientific, 13778-500), inverted phase contrast microscope (Nikon ECLIPSE Ti Microscope), laser confocal microscope (Nikon A1 Spectral Confocal Microscope), anoxic chamber (Coy Laboratory Products).

Antibodies used in Western blotting: Hexokinase 1 antibody (Abcam, 150423), Hexokinase 2 antibody (CST, 2867s), Hexokinase 3 antibody (Santa Cruz, sc-28890), α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments.

b) RNA interference: Cells were inoculated to a 35 mm culture dish for 24 hours. Short-interfering RNAs (siRNAs) were transfected with RNAiMAX Reagent. Scrambled RNA was used as a control. In total, 50 nM siRNAs were transfected into the cultures, and after 12 hours, the medium was replaced with fresh medium. Cells were then stimulated with hypoxia for 24 hours to detect the expression level of the indicated proteins.

Results

As shown in FIGS. 4A-4D, neither HK1 nor HK3 knockdown was capable of blocking microglial activation.

(3) Pyruvate Kinase M2 Subtype (PKM2) Interference could not Inhibit Hypoxia-Induced Activation of Microglia Materials Mouse BV2 microglia cell line, high glucose DMEM medium (Gibco, 11965-118), fetal bovine serum (Gibco, 10099-141), siRNA fragments, siRNA transfection reagent (Lipofectamine RNAiMAX Reagent, Thermo Fisher Scientific, 13778-500), inverted phase contrast microscope (Nikon ECLIPSE Ti Microscope), laser confocal microscope (Nikon A1 Spectral Confocal Microscope), anoxic chamber (Coy Laboratory Products).

Antibodies used in Western blotting: PKM2 antibody (Abcam, 150423), CD 11b antibody (Novus biologicals, NB 110-89474), α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity 95%), and observed under inverted microscope. Passage was performed approximately 2-3 days, and logarithmic growth phase cells were used for formal experiments.

b) RNA interference: Cells were inoculated to a 35 mm culture dish for 24 hours. Short-interfering RNAs (siRNAs) were transfected with RNAiMAX Reagent. Scrambled RNA was used as a control. In total, 50 nM siRNAs were transfected into the cultures, and after 12 hours, the medium was replaced with fresh medium. Cells were then stimulated with hypoxia for 24 hours to detect the expression level of the indicated proteins.

Results

Figure 5:
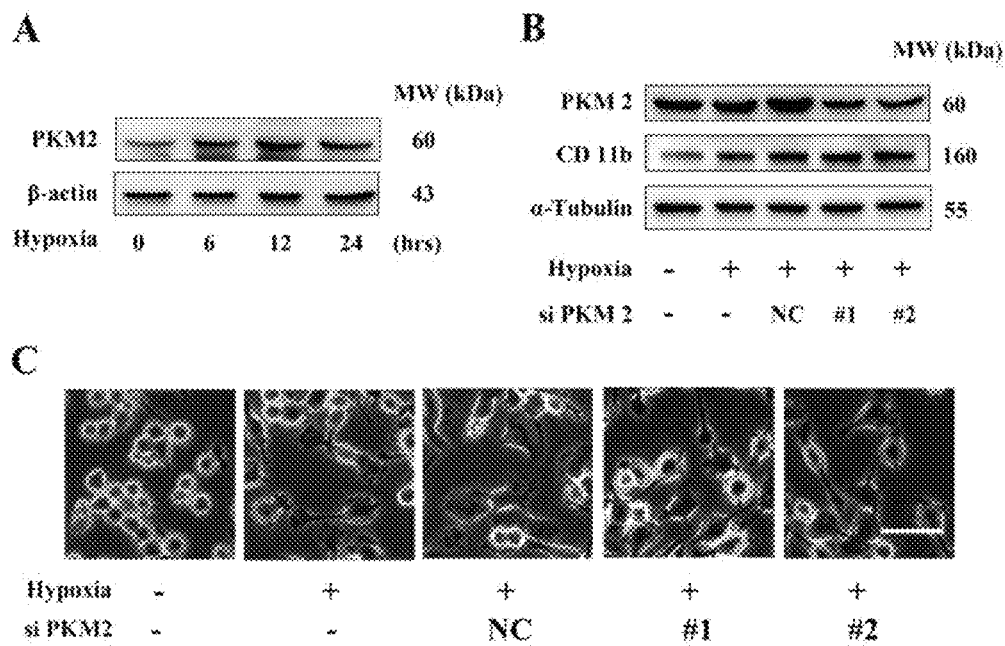
FIG. 5. PKM2 interference could not inhibit hypoxia-induced activation of microglia. (A) Immunoblot analysis of PKM2 protein expression in hypoxia-stimulated BV 2 cells. (B) PKM2 knockdown did not affect hypoxia-induced up-regulation of CD 11b. (C) Representative images showing that PKM2 knockdown could not repress the morphological changes induced by hypoxia. Scale bar, 50 μm.

Results showed PKM2 protein expression exhibited transient increases in hypoxia-stimulated BV 2 cells (FIG. 5A). Surprisingly, morphological changes induced by hypoxia was not inhibited by PKM2 knockdown (FIG. 5B-C).

(4) Lonidamine, a Hexokinase 2 Inhibitor, was Effective to Inhibit the Activation of Microglia Induced by Hypoxia.

Materials

Mouse BV2 microglia cell line, primary cultured mouse microglia, high glucose DMEM medium (Gibco, 11965-118), fetal bovine serum (Gibco, 10099-141), Lonidamine (Selleck, S2610), inverted phase contrast microscope (Nikon ECLIPSE Ti Microscope), laser confocal microscope (Nikon A1 Spectral Confocal Microscope), anoxic chamber (Coy LABORATORY PRODUCTS). Antibodies used in Western blotting: CD 11b antibody (Novus biologicals, NB 110-89474), α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments.

For the isolation and culture of primary microglia, cells were isolated from newborn C57BL/6J mice. Briefly, cerebral cortices devoid of meninges and blood vessels were dissociated from P0-2 mice and digested by 0.125% trypsin at 37° C. for 15 minutes. The digestion was terminated by addition of DMEM containing 10% FBS and isolated single cells were seeded in culture dishes. After the mixed cultures became confluent, microglia were separated from other cell types by slight shaking and purification was identified by the microglial-specific marker CD 11b.

b) CD 11b expression detected by Immunofluorescence: BV2 cells were seeded in a laser confocal-specific culture plate, and treated with hypoxia for 24 hours, fixed in 4% paraformaldehyde at room temperature for 20 minutes, and then washed three times with PBST for 5 minutes each time. After washing, CD 11b antibody diluted with DAKO antibody dilution was added and incubated overnight at 4° C. The next day, the samples were incubated with indicated fluorescently labeled secondary antibody at 37° C. for 1 hour. After the incubation, DAPI working solution was added for nuclear staining for 10 minutes. Samples were then washed three times with PBST and imaged using a laser confocal microscope.

Results

Figure 6:
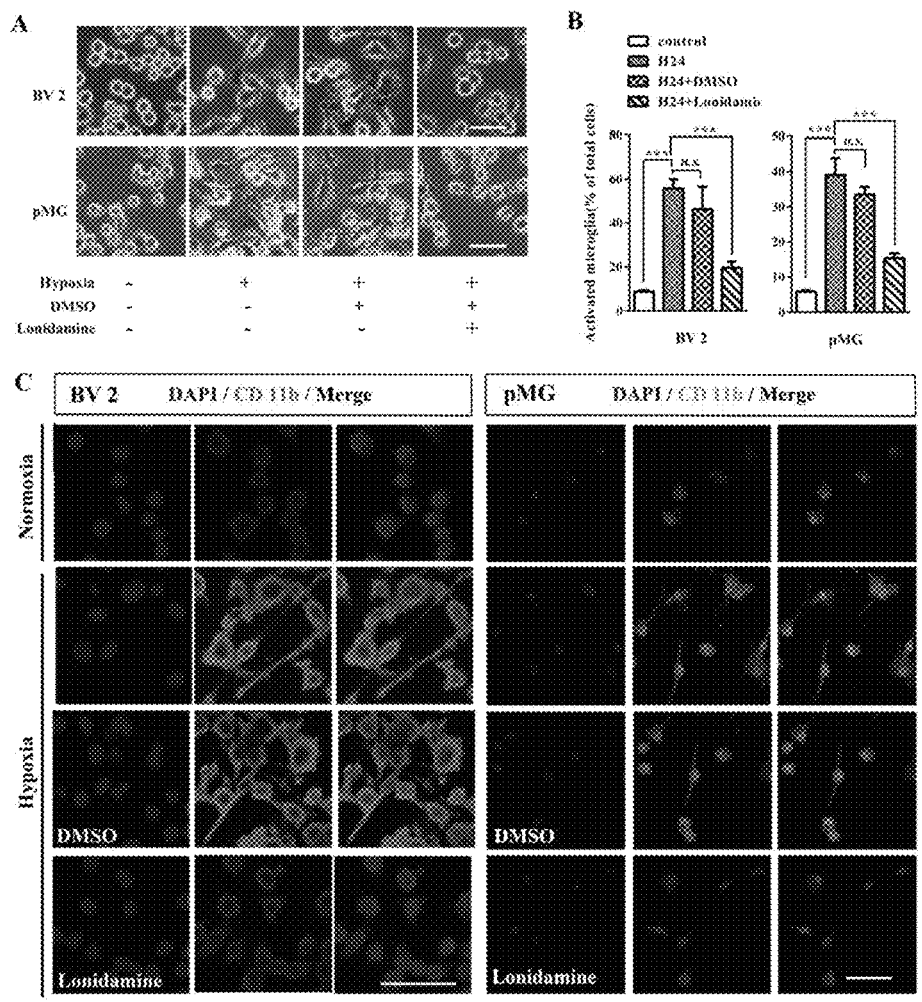
FIG. 6. Lonidamine, a HK2 inhibitor, could effectively inhibit hypoxia-induced activation of microglia. (A) The activated states of pMG and BV 2 cultures were markedly inhibited in the presence of lonidamine (50 μM) during hypoxia. Scale bar, 50 μm. (B) Graphs showing the diminished percentages of activated microglial cells treated with lonidamine in (A). (C) Immunofluorescence assay illustrating the reduction in CD 11b expression in the presence of lonidamine in BV 2 and pMG cells with hypoxia stimulation. Scale bar, 50 μm. *<0.05; <0.01; *<0.001.

Hypoxia stimulation led to profound morphological changes in BV 2 and pMG cells, as well as an enhanced expression of CD 11b (FIGS. 6A-B). Immunofluorescence assay illustrated the reduction in CD 11b expression in the presence of lonidamine (50 μM, DMSO as solvent), while DMSO as control had no effect on CD 11b expression.

Example 4 Hexokinase 2 Induction LED to Increased Histone Acetylation and Translational Activation of Il1b Materials Mouse BV2 microglia cell line, primary cultured mouse microglia, high glucose DMEM medium (Gibco, 11965-118), fetal bovine serum (Gibco, 10099-141), lonidamine (Selleck, S2610), 3-bromopyruvate (Sigma, 16490), RNA extraction reagent TRIzol (Thermo Fisher Scientific, 15596-018), RNA quantification kit (Thermo Fisher Scientific, Q10211), SuperReal qPCR PreMix (SYBR Green) (Tiangen, FP202-01), real-time PCR system (Applied Biosystems), chromatin immunoprecipitation kit (Millipore, 17-245), anoxic chamber (Coy Laboratory Products), inverted phase contrast microscope (Nikon ECLIPSE Ti Microscope). Antibodies used in Western blot: acetyl-Histone H3 antibody (Millipore, 06-599); acetyl-Histone H4 antibody (Millipore, 06-866); α-Tubulin antibody (Bioworld, AP0064).

Methods a) Cell culture: BV2 cells were grown in DMEM containing 10% fetal bovine serum (FBS), placed in 5% $CO_2$, cultured in a 37° C. constant temperature incubator (relative humidity was 95%), and observed under inverted microscope. Passage was performed approximately 2-3 days, and logarithmic growth phase cells were used for formal experiments.

For the isolation and culture of primary microglia, cells were isolated from newborn C57BL/6J mice. Briefly, cerebral cortices devoid of meninges and blood vessels were dissociated from P0-2 mice and digested by 0.125% trypsin at 37° C. for 15 minutes. The digestion was terminated by addition of DMEM containing 10% FBS and isolated single cells were seeded in culture dishes. After the mixed cultures became confluent, microglia were separated from other cell types by slight shaking and purification was identified by the microglial-specific marker CD 11b.

b) Total protein extraction and acetylated histone expression assay: Cells were incubated in a 35 mm culture plate for 24 hours, and stimulated with hypoxia for indicated time. The total protein was then extracted to detect protein expressions of acetylated histone.

c) Metabolite profiling: BV2 cells were seeded in a 60 mm culture dish and cultured for 24 hours and then cultured in normoxic or hypoxic conditions for 6 hours. Metabolites were extracted using 1.5 mL of ice-cold 80% methanol. After incubation at −80° C. for 30 minutes, cells were scrapped and centrifuged at 14,000 g for 15 min at 4° C. The upper methanol/water phase were transferred into new tubes and incubated at −80° C. for another 30 minutes. The upper phases were centrifuged and dried under nitrogen gas and dried samples were stored at −80° C. prior to LC-MS analysis.

d) Chromatin immunoprecipitation (ChIP) assay: BV 2 cells were treated with dimethylsulfoxide or lonidamine for 1 hour prior to 6 hours hypoxic exposure. Then, cells were cross-linked with a 1% formaldehyde solution (Sigma, F8775) for 10 minutes at 37° C. Cell lysates were sonicated to generate 100-1000 bp DNA fragments. Samples were diluted, and 10% of the total amount was retained for input. The remaining portions of each sample were pre-cleared, and anti-H3 or anti-H4 antibodies were added; a normal rabbit IgG antibody was simultaneously used as the negative control. The next day, protein G agarose was added and samples were washed after 2 hours of incubation. Cross-links were then reversed by incubation at 65° C. for 4 hours in 0.2 M NaCl. DNAs were extracted from the input and IP samples, and qPCR assays were performed. The Il1b promoter primer sequences were as follows: 5'-AGGTCAAAGGTTTGGAAGCAG-3' (forward) (SEQ ID NO. 19) and 5'-ATGGAAGTCTGTCTGCTCAGTATTG-3' (reverse) (SEQ ID NO. 20).

Results

Figure 7:
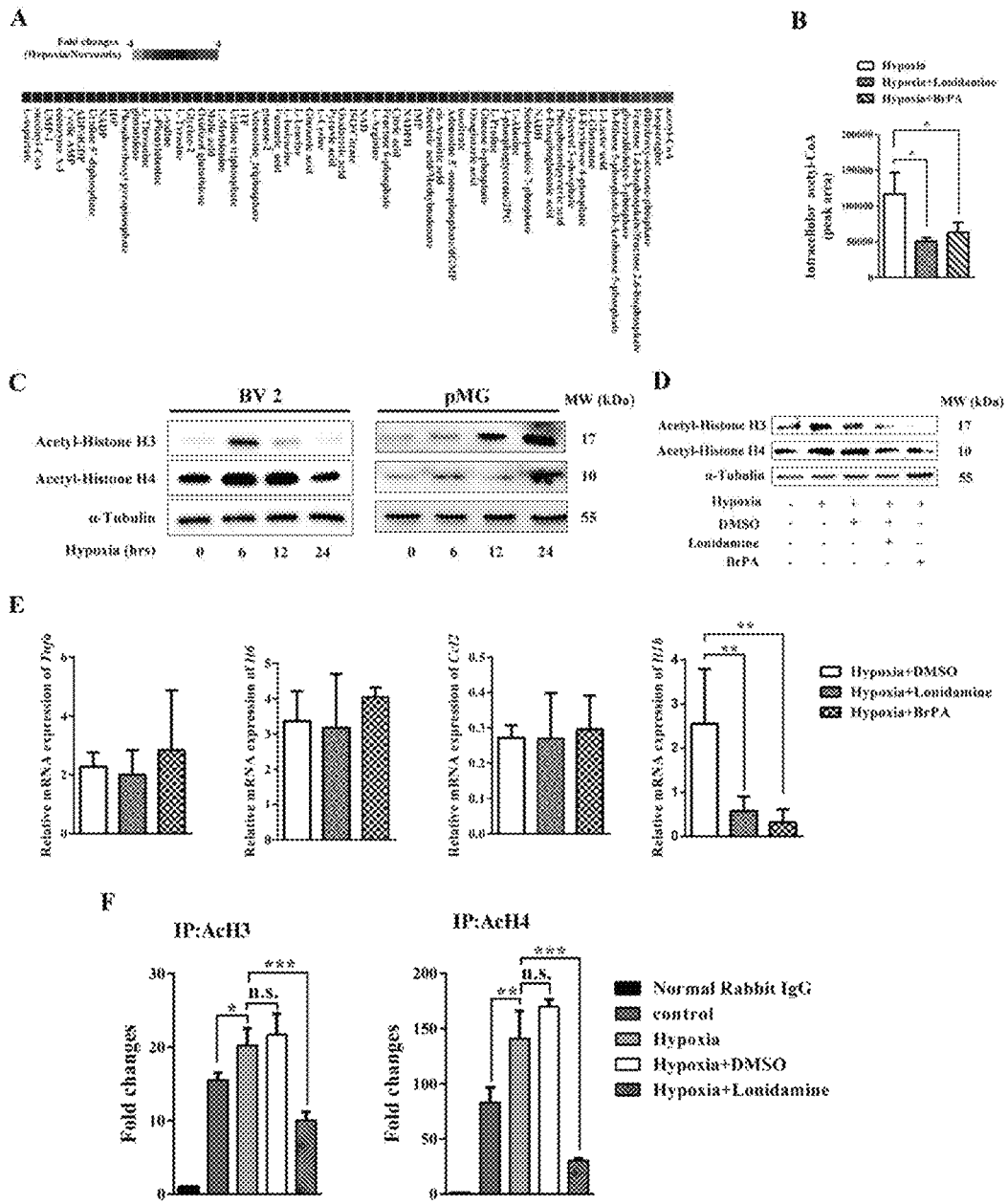
FIG. 7. HK2 induction leads to elevated level of histone acetylation and transcriptional activation of the proinflammatory cytokine (A) Metabolite profiling of the glycolysis and TCA cycle after BV 2 cells were exposed to a hypoxia for 6 hours. The data are presented as the fold changes of hypoxia versus normoxia. Down regulated ones are represented by green squares and up-regulated ones by red squares (n=4). (B)(D) HK2 inhibition reversed intracellular acetyl-CoA accumulation and inhibited up-regulated acetylated histones in BV 2 cells (n=4). (C) Expression levels of histone acetylation after hypoxia exposure in BV 2 and primary microglia (pMG) cells (n=3). (E) The hypoxia-induced up-regulation of Il1b at the mRNA level could be significantly decreased by HK2 inhibition (n=3). (F) Lonidamine pretreatment decreased the association of AcH3 and AcH4 with the Il1b promoter. The abundance of Il1b promoter with AcH3 or AcH4 in each treatment group was relative to the corresponding input samples with the same primer (n=3). *<0.05; <0.01; *<0.001.

As shown in FIG. 7A, after hypoxia stimulation for 6 hours, metabolic changes in the glycolysis, TCA cycle and pentose phosphate pathways were observed, in which acetyl-coenzyme A was most significantly affected by hypoxia. In the presence of HK2 inhibitors, lonidamine (50 μM) and 3-Br-pyruvate (BrPA, 10 μM), the hypoxia-induced accumulation of acetyl-coenzyme A were remarkably impaired (FIG. 7B). As shown in FIG. 7C, the acetylated histones 3 and 4 were transiently or continuously up-regulated in BV 2 and pMG cells over the time of hypoxia exposure. In BV 2 cells, the hypoxia-induced accumulation of histone acetylation was also reversed by HK2 inhibitors (FIG. 7D).

Next, quantitative reverse transcription polymerase chain reaction assays were performed to examine the mRNA levels of several proinflammatory cytokines in the presence or absence of HK2 inhibitors. Lonidamine (50 μM) and 3-BrPA (10 μM) dramatically inhibited hypoxia-induced Il1b expression at the mRNA level but had no effect on Tnfa and Il6 expression. Chromatin immunoprecipitation assays were carried out to examine endogenous binding of acetylated histones to Il1b promoter. The binding of AcH3 and AcH4 to the Il1b promoter increased during hypoxia, whereas it could be decreased by pretreatment with lonidamine (FIG. 7F).

Example 5. Hexokinase 2 Blockade Prevented Ischemic Brain Injury Through Repressing Microglia-Mediated Neuroinflammation in an Experimental Stroke Model (1) Lonidamine Protected the Brain from Ischemic Injury in a Rat MCAo Model Materials Lonidamine (Selleck, S2610), healthy male SPF Spague-Dawley (SD) rats, 2,3,5-TriphenylTetrazolium Chloride (TTC) (analytically pure), chloral hydrate (analytical grade) (purchased from Tianjin Kemiou Chemical Reagent Co., Ltd.), MCAo nylon monofilament.

Methods a) Middle Cerebral Artery Occlusion (MCAO) model was established by intraluminal thread technique from the right Internal Carotid Artery. Before surgery, SD rats were fasted for 12 hours, but with free access to drinking water. Animals were anesthetized by intraperitoneal injection of 10% chloral hydrate, and placed in a supine position on a 37° C. thermostatic operating table to maintain a smooth breathing. Under the operating microscope, the right CCA was exposed through a midline incision and occluded with a microvascular clip. The right external carotid artery was exposed and ligated at the distal end. A loose knot was made between the right common carotid artery bifurcation and the anterior external carotid artery ligature. The right internal carotid artery was dissected and clamped with a microvascular clip. A microscopic ophthalmic surgical scissors was used to cut a small opening between the two ligatures, and the nylon thread was insert down to the common carotid artery. Then the loose knot was tightened, and the right external carotid artery was cut under the distal ligation of the external carotid artery but above the suture insertion point. The microvascular clip at the internal carotid artery was then withdrawn, and the insertion end of the thread was placed at the bifurcation of the right common carotid artery. The external carotid artery was pulled outward and downward so that it was in line with the internal carotid artery. A nylon monofilament suture was inserted into the internal carotid artery until a mild resistance was felt. To prevent bleeding, the thread was tightened. The microvascular clip was withdrawn and the incision was sutured. Two hours after the operation, lonidamine or the indicated solvent control was administered at 10 mg/kg, and then the thread was withdrawn, and the cerebral infarction volume was measured 24 hours after the perfusion.

b) Infarct volume measurement: The rats were decapitated and brains were quickly removed and placed in iced saline for 10 minutes. Brain tissues were frozen and sliced into coronal sections (2-mm thick). The sections were then incubated in 1.0% 2,3,5-triphenyltetrazolium chloride (TTC) at 37° C. for 30 minutes and fixed in a 4.0% paraformaldehyde solution overnight. For each coronal slice, the infarct tissue (unstained area) and total bihemispheric area were delineated in the scanned image with Adobe Photoshop CS6. The infarcted volume was calculated as the ratio of the total unstained areas (white) over the total bihemispheric area.

Results

Figure 8:
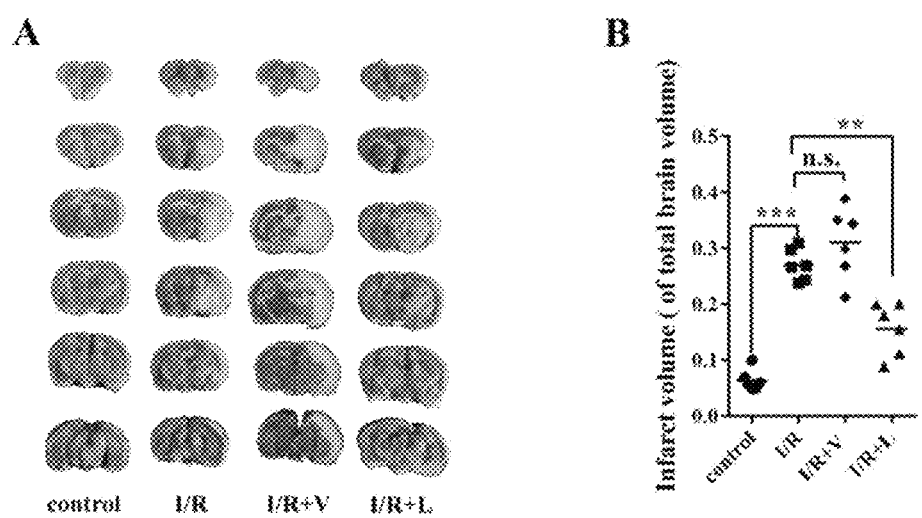
FIG. 8. Lonidamine effectively protected rats from brain damage caused by middle cerebral artery occlusion (MCAo). (A) Representative images of 2,3,5-triphenyltetrazolium chloride (TTC)-stained brain sections in each treatment group. (B) Quantification of infarct size in each group showing lonidamine administration significantly reduced the size of infarcts caused by MCAo. (n=6 per group) *<0.05; <0.01; *<0.001.

As shown in FIG. 8A, by TTC staining, obvious infarct area was observed 24 hours after 2 hours of cerebral ischemia-reperfusion in both MCAo rats and control group. Lonidamine administration significantly reduced the infarct size. 10 mg/kg lonidamine could effectively protect rat brains from ischemic damage (FIG. 8B).

(2) In Vivo Hexokinase 2 Knockdown Effectively Protected Rats from Brain Damage in a Rat MCAo Model Materials Lonidamin (Selleck, S2610), healthy male SPF Spague-Dawley (SD) rats, 2,3,5-TriphenylTetrazolium Chloride (TTC) Analytically pure, chloral hydrate (analytical grade) (purchased from Tianjin Kemiou Chemical Reagent Co., Ltd.), MCAo nylon suture, recombinant adeno-associated virus serotype 9 carrying shHK2 fragment (rAAV-shHK2), recombinant adeno-associated virus serotype 9 carrying scrambled control fragments (rAAV-shNC), immunohistochemistry kit (Abcam, ab80436), brain stereotaxic system, inverted phase contrast microscope (Nikon ECLIPSE Ti Microscope), laser confocal microscope (Nikon A1 Spectral Confocal Microscope).

Methods a) Middle Cerebral Artery Occlusion (MCAO) model was established by intraluminal thread technique from the right Internal Carotid Artery. Before surgery, SD rats were fasted for 12 hours, but with free access to drinking water. Animals were anesthetized by intraperitoneal injection of 10% chloral hydrate, and placed in a supine position on a 37° C. thermostatic operating table to maintain a smooth breathing. Under the operating microscope, the right CCA was exposed through a midline incision and occluded with a microvascular clip. The right external carotid artery was exposed and ligated at the distal end. A loose knot was made between the right common carotid artery bifurcation and the anterior external carotid artery ligature. The right internal carotid artery was dissected and clamped with a microvascular clip. A microscopic ophthalmic surgical scissors was used to cut a small opening between the two ligatures, and the nylon thread was insert down to the common carotid artery. Then the loose knot was tightened, and the right external carotid artery was cut under the distal ligation of the external carotid artery but above the suture insertion point. The microvascular clip at the internal carotid artery was then withdrawn, and the insertion end of the thread was placed at the bifurcation of the right common carotid artery. The external carotid artery was pulled outward and downward so that it was in line with the internal carotid artery. A nylon monofilament suture was inserted into the internal carotid artery until a mild resistance was felt. To prevent bleeding, the thread was tightened. The microvascular clip was withdrawn and the incision was sutured. Two hours after the operation, lonidamine or the indicated solvent control was administered at 10 mg/kg, and then the thread was withdrawn, and the cerebral infarction volume was measured 24 hours after the perfusion.

b) Infarct volume measurement: The rats were decapitated and brains were quickly removed and placed in iced saline for 10 minutes. Brain tissues were frozen and sliced into coronal sections (2-mm thick). The sections were then incubated in 1.0% 2,3,5-triphenyltetrazolium chloride (TTC) at 37° C. for 30 minutes and fixed in a 4.0% paraformaldehyde solution overnight. For each coronal slice, the infarct tissue (unstained area) and total bihemispheric area were delineated in the scanned image with Adobe Photoshop CS6. The infarcted volume was calculated as the ratio of the total unstained areas (white) over the total bihemispheric area.

c) Recombinant adeno-associated virus (rAAV) vectors were produced in 293T cells. The genomic titers of the viruses ranged from $3.2 \times 10^{12}$ to $3.5 \times 10^{12}$ V.G./mL, as determined by qPCR. To construct the AAV2/9 vectors, the following sequences targeting HK2 were used: 5'-GCGCAACATTCTCATCGATTT-3' (SEQ ID NO. 21) and 5'-AAATCGATGAGAATGTTGCGC-3' (SEQ ID NO. 22). The control shRNA sequence was 5'-TTCTCCGAACGTGTCACGT-3' (SEQ ID NO. 23). In total, 2 μL of the viral vectors were injected unilaterally into the striata of anesthetized rats fixed in a stereotaxic frame. The injection site coordinates were: 1.0 mm rostral to bregma, 3.0 mm lateral to the midline, and 4.5 mm ventral to the dura, with the tooth bar set to zero. Microinjections were carried out at a rate of 0.2 μL/minutes. After injection, the microsyringe remained in situ for an additional 5 minutes before being withdrawn.

d) Tissue immunofluorescence was used to detect the distribution of virus in the brain (eGFP), and expressions of hexokinase 2 and Iba-1 (another molecular marker of microglia activation): After ischemia for 2 hours and reperfusion for 24 hours, the intact brain tissue was removed by anesthesia and embedded in paraffin-embedded to obtain sections. The thickness of the brain slices was approximately 4 μm. The brain slices were deparaffinized and hydrated, and subjected to antigen retrieval. Samples were incubated in indicated antibodies at 4° C. overnight. The next day, the fluorescently labeled secondary antibody was added and samples were incubated at 37° C. for 1 hour. After the incubation, DAPI working solution was added for nuclear staining for 10 minutes. At the end of the treatment, samples were washed three times with PBST and imaged using a laser confocal microscope.

e) Immunohistochemical detection of IL-1β expression: After ischemia for 2 hours and reperfusion for 24 hours, the intact brain tissue was removed by anesthesia and embedded in paraffin-embedded to obtain sections. The thickness of the brain slices was approximately 4 μm. The brain slices were deparaffinized and hydrated, and subjected to antigen retrieval. Samples were incubated in indicated primary antibodies overnight at 4° C. The next day, samples were washed in phosphate-buffered saline, subjected to serial incubation in complement and a horseradish peroxidase (HRP) conjugate. After incubating for 15 minutes at room temperature, samples were incubated with DAB developing solution for 1 minute. Finally, samples were stained with hematoxylin and imaged using a Nikon microscope.

Results

Animal weights were monitored constantly, and no statistical significance was detected 20 days after rAAV9-shHK2 and rAAV9-shNC injections. (Animal weights in the AAV2/9-shNC and AAV2/9-shHK2 groups were 273.2±6.9 g and 269.3±5.0 g, respectively). Before surgery, whole-brain tissues from rats were collected to detect the spread of AAVs using in vivo optical imaging technology based on eGFP expression (FIG. 9A). Staining slices of brain showed that HK2 is significantly up-regulated by MCAo surgery. Because of the disseminated distribution of AAVs, however, the HK2 up-regulated by MCAo surgery was effectively inhibited in rAAV9-shHK2 group, whereas rAAV9-shNC injection had no significant effect on HK2 inhibition (FIG. 9B). Similar to HK2 inhibition, TTC staining showed infarct sizes reduced significantly in HK2-knockdown rats compared to their counterparts injected with AAVs carrying control shRNA (FIG. 9C-D).

Figure 9:
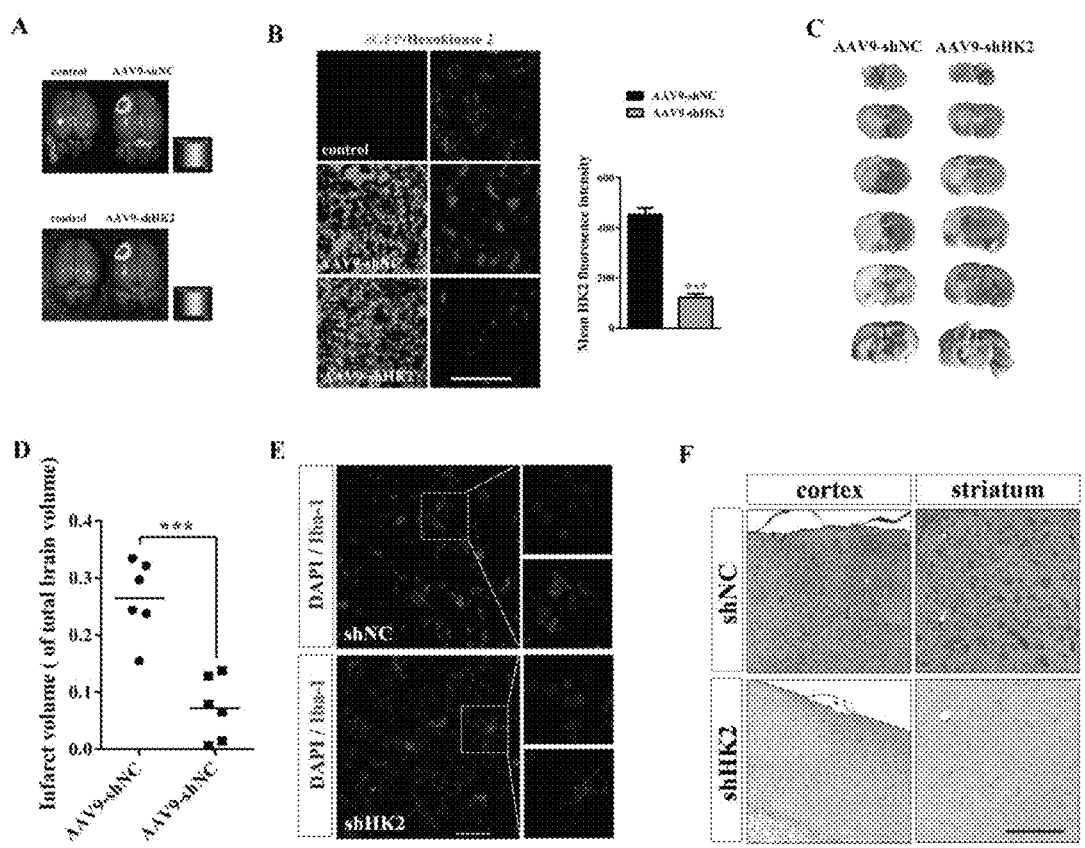
FIG. 9. In vivo HK2 knockdown effectively protected rats from brain damage caused by middle cerebral artery occlusion (MCAo). (A) Virus distribution was monitored using whole-brain imaging based on eGFP expression 21 days after the injection of AAV vectors (n=3). (B) Brain sections in the striata stained for HK2 and CD 11b showing that CD 11b was positively correlated with HK2 expression in microglia (n=6/group). Scale bar, 20 μm. (C) TTC staining showing reduced infarct size in the AAVshHK2 treated group after MCAo surgery (n=6/group). (D) Quantification of the infarct size in (c) (n=6/group). (E) Iba-1 immunoreactivity in the striatum showing that AAV-shHK2 treatment dramatically inhibited microglial activation in the infarct hemisphere. Scale bar, 50 μm. (F) Representative images taken from cortices and striata in the ischemic hemispheres showing reduced IL-1b production after AAV2/9-shHK2 treatment in the rat MCAo model. *<0.05; <0.01; *<0.001.

As revealed in FIG. 9E, microglia in the rAAV9-shNC group had morphological characteristic of activated microglia, with the enlargement of cell bodies and retraction of projections, whereas their activated morphologies were markedly repressed in the shHK2 treatment group. The neuroprotective effect of HK2 knockdown was associated with the prominent inhibition of Iba-1 expression (FIG. 9E). As depicted in FIG. 9, immunohistochemical staining of Il-1β in the cortex and striatum regions showed that the neuroprotection mediated by knockdown of endogenous hexokinase 2 is associated with decreased expression of Il-1β; in the control group, Il-1β is distributed in the cortex and striatum, whereas in the rAAV9-shHK2 group, the expression of Il-1β was significantly inhibited.

The invention claimed is:

1. A method for treatment of acute central nervous system injury mediated by microglia activation, comprising administering to a subject a pharmaceutically effective amount of lonidamine, wherein the acute central nervous system injury mediated by microglia activation comprises acute ischemic brain injury, ischemic stroke, acute cerebral infarction or lacunar infarction.

2. The method of claim 1, wherein the lonidamine is comprised in a composition.

3. The method of claim 2, wherein the composition further comprises one or more compounds selected from a group consisting of 2-deoxyglucose, bromopyruvic acid, glucose 6-phosphate, Imatinib, 5-thio-glucose and methyl jasmonate.

* * * * *